United States Patent [19]

Genese

[11] 4,237,880

[45] Dec. 9, 1980

[54] EQUIPMENT SETS FOR THE SEQUENTIAL ADMINISTRATION OF MEDICAL LIQUIDS AT DUAL FLOW RATES EMPLOYING A COMBINED AIR BARRIER AND LIQUID SEQUENCING VALVE CONTROLLED BY A COMMON FLEXIBLE MEMBRANE

[75] Inventor: Joseph N. Genese, Waukegan, Ill.

[73] Assignee: Abbott Laboratories, North Chicago, Ill.

[21] Appl. No.: 16,231

[22] Filed: Feb. 28, 1979

[51] Int. Cl.³ .................................................. A61M 5/14
[52] U.S. Cl. ................................. 128/214 G; 128/274; 222/129.2; 222/145; 137/113; 137/859
[58] Field of Search ............ 128/214 R, 214 C, 214 G, 128/214.2, 227, 274; 222/129.2, 145; 137/112–114, 589

[56] References Cited

U.S. PATENT DOCUMENTS

| Re. 25,211 | 7/1962 | Fellberg | 137/589 X |
|---|---|---|---|
| 3,196,890 | 7/1965 | Brandenberg | 137/112 X |
| 3,633,605 | 1/1972 | Smith | 137/113 |
| 3,886,937 | 6/1975 | Bobo et al. | 128/214 G |

*Primary Examiner*—Dalton L. Truluck
*Attorney, Agent, or Firm*—Robert L. Niblack; Aaron L. Hardt; Robert S. Beiser

[57] ABSTRACT

Equipment sets for the sequential administration of medical liquids wherein a primary liquid can be administered at a flow rate independent of the flow rate of a secondary liquid, and including a barrier substantially impervious to air to prevent the inadvertent administration of air when the secondary liquid is depleted. The sets of this invention employ a combined air barrier and liquid sequencing valve controlled by a common flexible membrane.

11 Claims, 5 Drawing Figures

EQUIPMENT SETS FOR THE SEQUENTIAL ADMINISTRATION OF MEDICAL LIQUIDS AT DUAL FLOW RATES EMPLOYING A COMBINED AIR BARRIER AND LIQUID SEQUENCING VALVE CONTROLLED BY A COMMON FLEXIBLE MEMBRANE

BACKGROUND OF THE INVENTION

The present invention relates to systems and equipment sets for the administration of medical liquids to a patient, and more particularly, to systems and equipment sets for the sequential administration of a plurality of medical liquids employing a combined air barrier and liquid sequencing valve controlled by a common flexible membrane.

The parenteral administration of medical liquids to patients is a long established practice. Liquids including amino acids, blood, dextrose, electrolytes, and saline are commonly administered to patients over prolonged periods of time. Generally, these liquids are administered from a glass bottle or plastic bag suspended above the patient and containing 250–2,000 ml. of the liquid. Such prolonged infusions commonly are administered at a flow rate of 10–150 ml./hr.

Frequently, the patient must receive an additive or secondary liquid while the prolonged infusion is being administered. Preferably, this secondary liquid should be administered through the same hypodermic needle to avoid unnecessary pain and trauma to the patient of additional venipunctures. To avoid dilution and incompatability problems, it is also preferable that the flow of the primary liquid employed in the prolonged infusion be temporarily interrupted, the secondary liquid administered and the flow of the primary liquid resumed. Generally, the secondary liquid will be administered at a flow rate of 50–250 ml./hr.

Abbott Laboratories, North Chicago, Ill. manufactures a y-type set for the sequential administration of primary and secondary liquids. These VENOSET piggyback sets allow the prolonged infusion of a primary liquid to be temporarily halted by means of a backcheck valve in the primary liquid flow path to administer a secondary liquid without the need for a new venipuncture. Then, when the secondary liquid has been depleted, the backcheck valve automatically opens to resume flow of the primary liquid. An important characteristic of this system is that the secondary liquid container must be suspended at a higher height than the primary liquid container to establish the liquid pressure differential that closes the backcheck valve in the primary liquid flow path.

A similar system is disclosed in U. S. Pat. No. 3,886,937 granted June 3, 1975 to D. Bobo, et al., assigned to American Hospital Supply Corp., and entitled "Medical Administration Set for Dispensing Plural Medical Liquids". Another similar system is disclosed in U.S. Pat. No. 4,105,029 granted Aug. 8, 1978 to R. Virag, assigned to Baxter Travenol and entitled "Intravenous Solution Set Having An Air Access Site and Constricted Inner Diameter Portion".

An inherent disadvantage of the above-mentioned prior art medical liquid administration systems is that they each resume the flow of primary liquid at the rate the secondary liquid had been flowing. Because the preferred flow rate of the secondary liquid is generally greater than the preferred flow rate of the primary liquid, when the primary liquid resumes flow at that rate, the patient can be administered an excessive amount of primary liquid, unless the flow rate of the primary liquid is adjusted to the preferred primary liquid flow rate soon after the flow of primary liquid resumes.

A remedy to the above-described disadvantage would appear to be provided by simply incorporating flow control devices into both the primary and secondary liquid flow paths. However, while this remedy does provide dual flow rates for the primary and secondary liquids, it is unacceptable. That is, because the common tube of the y-set must be able to accommodate both flow rates, when the primary liquid is flowing at a slower rate than the secondary liquid was, there will be an unfilled volume or void in the common tube. To fill that void, air will be drawn into the common tube from the depleted secondary container. That air will then be driven into the patient by the weight of the primary liquid, thereby causing a serious embolism and perhaps, the patient's death.

Accordingly, it will be apparent that an efficacious equipment set for the sequential administration of medical liquids at dual flow rates would be advantageous to the medical profession.

SUMMARY OF THE INVENTION

The primary object of the present invention, therefore, is to provide equipment sets for the sequential administration of medical liquids at dual flow rates that will not draw air from the secondary container when the secondary liquid has been depleted.

In accordance with this and other objects, there is provided by the present invention equipment sets for the sequential administration of medical liquids to a patient including a primary tube, a secondary tube, and a common tube all connected in fluid communication to form a primary liquid flow path and a secondary liquid flow path. The primary liquid flow path includes the primary and common tube, while the secondary liquid flow path includes the secondary and common tubes.

To establish the dual flow rates of the primary and secondary liquids, a secondary flow control means in the secondary liquid flow path for adjusting the flow rate of the secondary liquid and a primary flow control means on the primary tube for adjusting the flow rate of the primary liquid to a rate independent of the flow rate of the secondary liquid are provided.

A combined air barrier and liquid sequencing valve provides a first chamber which constitutes a portion of the primary tube and has inlet and outlet ports thereto and a second chamber which constitutes a portion of the secondary tube and has inlet and outlet ports thereto. The housing of the combined air barrier and liquid sequencing valve is divided into the first and second chambers by a common flexible membrane which normally covers a port of the second chamber, but is adapted to flex away from that port and cover a port of the first chamber whenever the pressure of secondary liquid in the second chamber exceeds the pressure of primary liquid in the first chamber. Thus, primary liquid is allowed to flow from the primary container whenever the height of primary liquid is greater or equal to the height of secondary liquid in the system and prevented from flowing whenever the height of primary liquid is less than the height of secondary liquid. When the diaphragm covers the port of the second chamber, it provides a substantially impervious barrier to air to insure that no air is drawn from the secondary container when the secondary liquid is depleted.

BRIEF DESCRIPTION OF THE DRAWING

Other objects and attendant advantages will become obvious to those skilled in the art by reading the following detailed description in connection with the accompanying drawing, wherein like reference characters designate like or corresponding parts throughout the several figures thereof and wherein.

DETAILED DESCRIPTION OF THE INVENTION

Figure 1:
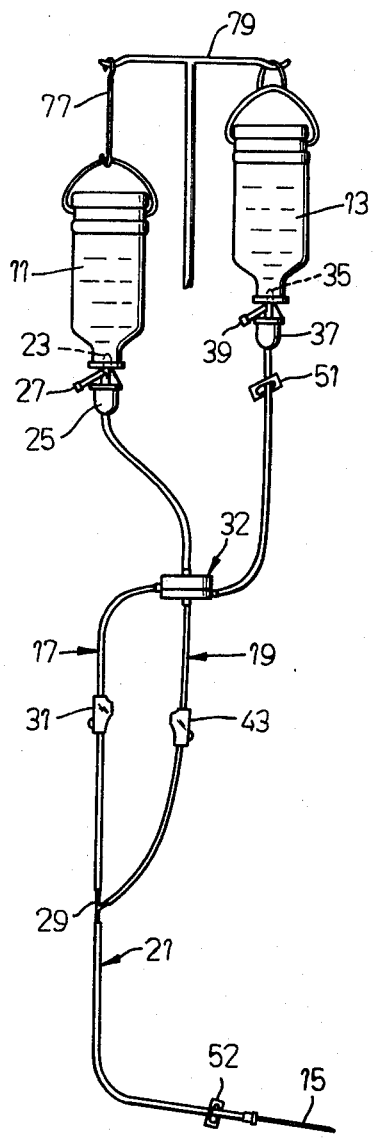
FIG. 1 is a front elevational view of an equipment set for the sequential administration of medical liquids at dual flow rates contemplated by this invention.

Referring to the drawing, there is shown in FIG. 1, the basic elements of the equipment sets for the sequential administration of medical liquids at dual flow rates contemplated by this invention. FIG. 1 depicts a primary liquid container 11 that contains a primary medical liquid to be administered to a patient for a prolonged period of time. FIG. 1 also depicts a secondary liquid container 13 that contains a secondary medical liquid to be administered to the patient for a relatively short period of time, during which time the administration of the primary liquid will be temporarily interrupted. Containers 11 and 13 can be glass bottles, plastic flexible bags, or any other suitable container.

Primary container 11 and secondary container 13 are connected in fluid communication to a conventional hypodermic needle 15 through a primary tube 17, a secondary tube 19, and a common tube 21. Thus, the primary liquid flow path from primary container 11 to needle 15 comprises primary tube 17 and common tube 21. Likewise, the secondary liquid flow path from secondary container 13 to needle 15 comprises secondary tube 19 and common tube 21.

The distal end of primary tube 17 is in fluid communication with primary container 11, preferably by means of a piercing pin 23 inserted into a puncturable closure of container 11. Piercing pin 23 can have an integral drip chamber 25, and when container 11 is a glass bottle, as shown in the set of FIG. 1, an integral, filtered air vent 27. Such piercing pins, drip chambers and air vents are well known in the medical practice and need not be more fully explained here.

The proximal end of primary tube 17 is joined in fluid communication to the distal end of common tube 21, preferably by a y-tube 29, it being understood that the primary, secondary and common legs of y-tube 29 constitute a portion of the primary, secondary and common tubes 17, 19 and 21, respectively. Primary tube 17 has a primary flow control 31 at any convenient location intermediate its ends for independently adjusting the rate of flow of the primary liquid through the primary liquid flow path. Preferably, as shown in FIG. 1, primary flow control 31 can be a roller clamp. However, it can be any other adjustable device that will reliably maintain a desired primary liquid flow rate.

Figure 4:
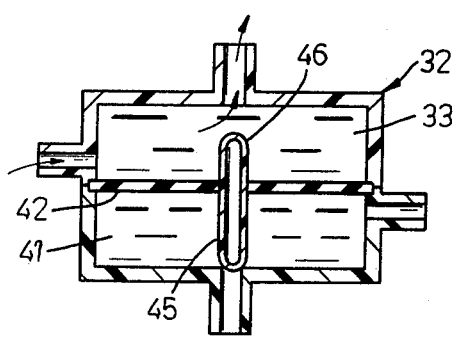
FIGS. 4-5 are front elevational views in cross-section illustrating the operation of another combined air barrier and liquid sequencing valve contemplated by this invention.

The distal end of secondary tube 19 is in fluid communication with secondary container 13, preferably, by means of a piercing pin 35 inserted into a puncturable closure of container 13. Piercing pin 35 can have an integral drip chamber 37, and when container 13 is a glass bottle, as shown in FIG. 1, an integral, filtered air vent 39. The proximal end of secondary tube 19 is joined in fluid communication to the distal end of common tube 21, preferably, by a y-tube 29. When the device of FIG. 4 is employed in the set of FIG. 1, the proximal end of secondary tube 19 is detachably joined to the distal end of common tube 21.

A secondary flow control 43 is disposed at any convenient location in the secondary liquid flow path. Preferably, as shown in FIG. 1, secondary flow control 43 can be a roller clamp. However, it can be any other adjustable device that can reliably maintain a desired secondary liquid flow rate.

A combined air barrier and liquid sequencing valve having a housing 32 is shown in FIG. 1. Housing 32 has first and second chambers 33, 41, as shown in FIGS. 2-5, that are formed by an air and liquid impermeable flexible membrane 42. First and second chambers 33, 41 each have inlet and outlet ports thereto through housing 32 that are respectively connected in fluid communication to the other portions of the primary or secondary tubes 17, 19. It will be readily apparent to those skilled in the art, that either port of first chamber 33 can be employed as the inlet or outlet thereof, while either port of second chamber 41 can, likewise, be employed as the inlet or outlet thereof. Primary tube 17 thus includes first chamber 33 of housing 32, while secondary tube 19 includes second chamber 41.

Figure 2:
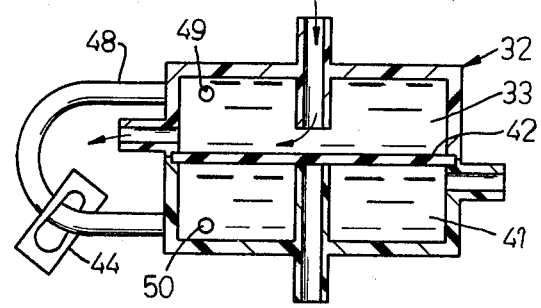
FIGS. 2-3 are front elevational views in cross-section illustrating the operation of a preferred combined air barrier and liquid sequencing valve.
Figure 3:
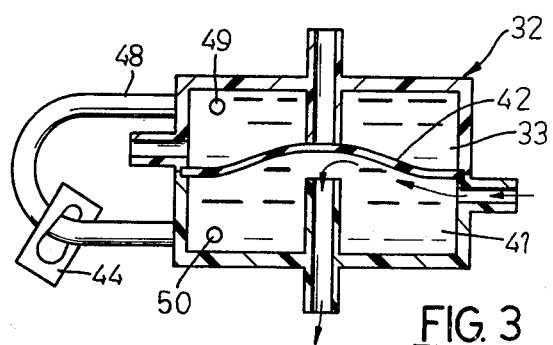
Figure 5:
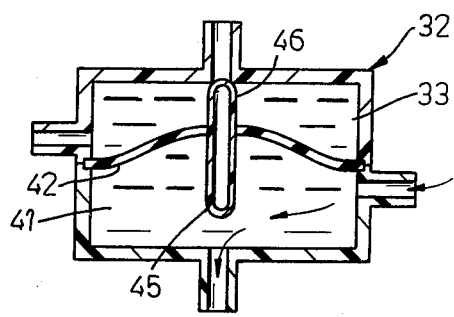

Flexible membrane 42 can be made of natural or silicone rubber, or thermoplastic materials such as polyethylene. Flexible membrane 42 can be captured between joined halves of housing 32, or alternatively, flexible membrane 42 can be insert molded into an integral housing 32. Flexible membrane 42 normally covers one port of second chamber 41, as shown in FIGS. 2 and 4. However, when the pressure of secondary liquid in second chamber 41 is greater than the pressure of primary liquid in first chamber 33, flexible membrane 42 will flex or hydrostatically move away from that port and cover one port of first chamber 33, as shown in FIGS. 3 and 5.

Thus, flexible membrane 42 allows primary liquid to flow from primary container 11 whenever the height of the primary liquid is greater than or equal to the height of the secondary liquid in the system of FIG. 1. Further, flexible membrane 42 prevents the flow of primary liquid from primary container 11 whenever the height of the primary liquid is less than the height of the secondary liquid in the system. When flexible membrane 42 covers the port of second chamber 41, it provides a barrier that is substantially impervious to air while the set is in use and prevents the flow of air through the secondary flow path.

As shown in FIG. 2, first chamber 33, preferably, has its inlet at the top and extends into first chamber 33 a substantial distance. Preferably, the outlet from first chamber 33 is on a side wall thereof. As shown in FIG. 2 also, the outlet from second chamber 41, preferably, is at the bottom and extends into second chamber 41 a substantial distance. Preferably, the inlet to second chamber 41 is on a side wall thereof.

The device of FIG. 2 is provided a priming tube 48 having a priming tube flow control means 44 thereon which controls the flow of liquid through priming tube 48. The ends of priming tube 48 are joined in fluid communication to orifices 49, 50 of first and second chambers 33, 41 respectively.

Alternatively, as shown in FIG. 4, flexible membrane 42 carriers stoppers 45, 46 that are aligned with the outlet to first chamber 33 and outlet from second chamber 41. As shown in FIGS. 4 and 5, when flexible membrane 42 is in its normal position, stopper 45 covers the outlet from second chamber 41 and stopper 46 covers the outlet to first chamber 33 when flexible membrane 42 is flexed or hydrostatically moved away from its normal position by the pressure of secondary liquid.

The set of FIG. 1 includes a slide clamp 51 near the distal end of secondary tube 19 and a slide clamp 52 near the proximal end of common tube 21.

For simplicity, the equipment sets of this invention have been depicted and described as integral units. It is apparent, however, that the sets can be manufactured and assembled in subsets of the entire set and that each subset will accordingly be provided such resealable closures, piercing means, adapters, etc. as are necessary to permit their easy assemblage into the complete set at an appropriate time.

OPERATION OF THE SYSTEM

As depicted in FIG. 1, primary container 11 is suspended in space at a height above the patient by means of a hook 77 and stand 79. It will be apparent that other means for suspending the containers of this invention are well known.

To insure that all the air that might be forced into the patient has been removed from the sets, the sets are initially primed by first closing slide clamps 51 and 52. Piercing pin 23 is then inserted into the resealable closure of primary container 11. If the device of FIG. 2 is being used, slide clamps 44, 51 and 52 and flow control 43 are then opened. Primary liquid will then flow into first chamber 33 until it is full, then through priming tube 48 into second chamber 41 until it is full, then out of chamber 41 into secondary tube 19. When primary liquid is about to reach the proximal end of secondary tube 19 slide clamp 52 is closed. When primary liquid is about to reach the distal end of secondary tube 19, slide clamp 51 is closed. Slide clamp 44 is then closed.

For either the device of FIG. 2 or 4, primary flow control 31 is now fully opened. Slide clamp 52 is opened to allow primary liquid to flow through the primary liquid flow path and force all the air therefrom that might be forced into the patient. The weight of primary liquid in chamber 33 on flexible membrane 42 will further bias membrane 42 against the outlet from second chamber 41. Slide clamp 52 is then closed. At this point, with the device of FIG. 4, secondary chamber 41 will still be empty and flow control 43 closed.

Common tube 21, which preferably has an adapter at its proximal end open to the flow of liquid therefrom, is next connected to needle 15, which will generally have been already inserted into a vein of the patient. Slide clamp 52 will then be opened to allow primary liquid to flow through the primary liquid flow path to the patient's vein. Primary flow control 31 is then adjusted to a setting that will provide the desired flow rate for a prolonged infusion of primary liquid into the patient, generally 10–150 ml./hr. As is well known in the medical practice, that flow rate can be visually observed by viewing and counting drops passing through the primary drip chamber 25.

Subsequently, when it is desired to administer a secondary liquid to a patient, piercing pin 35 at the distal end of secondary tube 19 will be inserted into the resealable closure of secondary container 13. When the device of FIG. 4 is in use, the proximal end of secondary tube 19 is then detached from y-tube 29, slide clamp 51 opened and secondary liquid allowed to flow through secondary tube 19 until it reaches the proximal end thereof. Slide clamp 51 is then closed and the proximal end of secondary tube 19 reattached to y-tube 29.

For either the device of FIG. 2 or 4, secondary container 13 is then suspended in space from stand 79 at a height substantially greater than the height of primary container 11 and slide clamp 51 is opened. Secondary liquid will then immediately begin to flow through the secondary liquid flow path. The pressure of secondary liquid on flexible membrane 42 is greater than the pressure of the primary liquid and will force the flexible membrane 42 away from the covered port of second chamber 41 against and over a port of first chamber 33 to prevent the flow of primary liquid from primary container 11. Secondary flow control 43 is then adjusted to a desired flow rate, typically 50–250 ml./hr., for the secondary liquid, which will then flow until the liquid in secondary container 13 is depleted.

When the height of primary liquid in the set of FIG. 1, becomes greater than the height of the secondary liquid, flexible membrane 42 will immediately move away from the covered port of first chamber 33 and allow primary liquid to flow from primary container 11 at the flow rate to which primary flow control 31 is adjusted. Flexible membrane 42 will then return to its normally closed position covering one port of second chamber 41 and providing a substantially impermeable barrier to air in the secondary liquid flow path.

When primary container 11 becomes depleted of primary liquid, the primary piercing pin 23 is merely removed therefrom and inserted into the resealable closure of a new primary container, which is then suspended in place of the previous container. If primary container 11 had completely emptied before it was replaced, it will be necessary to prime primary tube 17 in the manner by which it was initially primed.

When secondary container 13 becomes depleted of secondary liquid, it can be left empty until another secondary liquid is to be administered. When another secondary liquid is to be administered, the secondary piercing pin 35 is merely removed from secondary container 13 and inserted into a new secondary liquid container and the priming procedure used for initiating the flow of secondary liquid from the first secondary container repeated.

Having described the invention in specific detail and exemplified the manner in which it may be carried into practice, it will now be readily apparent to those skilled in the art that innumerable variations, applications, modifications and extensions of the basic principles involved may be made without departing from its sphere or scope.

I claim:

1. A set for the sequential administration of medical liquids to a patient, comprising:
    a primary tube for the flow of a primary medical liquid therethrough,
    a secondary tube for the flow of a secondary medical liquid therethrough;
    a common tube having its distal end in fluid communication with the proximal ends of said primary and secondary tubes and its proximal end open for the flow of liquid therefrom to form a primary liquid flow path comprising said primary tube and said common tube and a secondary liquid flow path comprising said secondary tube and said common tube, a secondary flow control means in said secondary liquid flow path for adjusting the flow rate of said secondary liquid therethrough, a primary flow control means on said primary tube for adjusting the flow rate of said primary liquid through said primary flow path to a rate independent of the flow rate of said secondary liquid through said secondary liquid flow path, and a combined air barrier and liquid sequencing valve having a housing comprising a first chamber which constitutes a portion of said primary tube and has inlet and outlet ports thereto and a second chamber which constitutes a portion of said secondary tube and has inlet and outlet ports thereto, said housing divided into said first and second chambers by an air and liquid impermeable flexible diaphragm, a portion of said diaphragm normally covering one of said ports to said second chamber and hydrostatically moveable away therefrom to cover one of said ports to said first chamber, whereby said flexible diaphragm prevents the flow of primary liquid through said primary tube whenever the pressure of said secondary liquid in said second chamber exceeds the pressure of said primary liquid in said first chamber and provides a barrier substantially impervious to air in said secondary liquid flow path whenever the pressure of said primary liquid in said first chamber exceeds the pressure of said secondary liquid in said second chamber.

2. The set defined in claim 1, wherein said first chamber has said inlet port at the top thereof and said outlet port at a side thereof and said second chamber has said inlet port at a side thereof and said outlet port at the bottom thereof, whereby said flexible diaphragm normally covers said outlet port to said second chamber and moves therefrom to cover said inlet port to said first chamber.

3. The set defined in claim 1, wherein said first chamber has said outlet port at the top thereof and said inlet port at a side thereof and said second chamber has said inlet port at a side thereof and said outlet port at the bottom thereof, whereby said flexible diaphragm normally covers said outlet port to said second chamber and moves therefrom to cover said outlet port to said first chamber.

4. The set defined in claim 1, 2 or 3, wherein said first chamber further includes an orifice joined in fluid communication to an orifice in said second chamber by a priming tube having a priming flow control means thereof for controlling the flow of liquid through said priming tube.

5. The set defined in claim 2, wherein said inlet port to said first chamber and said outlet port from said second chamber extend a substantial distance into their respective chambers.

6. The set defined in claim 3, wherein said outlet port from said first chamber and said outlet port from said second chamber extend a substantial distance into their respective chambers.

7. The set defined in claim 1, wherein said primary tube has a piercing pin at its distal end.

8. The set defined in claim 1 or 2, wherein said secondary tube has a piercing pin at its distal end.

9. The set defined in claim 8, wherein said piercing pins of said primary and secondary tube have drip chambers integral therewith.

10. The set defined in claim 8, wherein said piercing pins of said primary and secondary tube have air vents integral therewith.

11. The set defined in claim 1, 2, 3 or 4, wherein said proximal end of said secondary tube is detachably joined to said distal end of said common tube.

* * * * *

UNITED STATES PATENT AND TRADEMARK OFFICE
CERTIFICATE OF CORRECTION

PATENT NO. : 4,237,880

DATED : December 9, 1980

INVENTOR(S) : Joseph N. Genese

It is certified that error appears in the above–identified patent and that said Letters Patent are hereby corrected as shown below:

Column 8, Claim 4, line 17, first word should read "thereon"

Column 8, Claim 8, line 29, delete the numeral "2" and substitute the numeral "7".

Signed and Sealed this

Twenty-first Day of April 1981

[SEAL]

Attest:

RENE D. TEGTMEYER

Attesting Officer

Acting Commissioner of Patents and Trademarks